(12) United States Patent
Vitek et al.

(10) Patent No.: US 8,409,099 B2
(45) Date of Patent: Apr. 2, 2013

(54) FOCUSED ULTRASOUND SYSTEM FOR SURROUNDING A BODY TISSUE MASS AND TREATMENT METHOD

(75) Inventors: Shuki Vitek, Haifa (IL); Kobi Vortman, Haifa (IL)

(73) Assignee: Insightec Ltd., Tirat Carmel (IL)

( * ) Notice: Subject to any disclaimer, the term of this patent is extended or adjusted under 35 U.S.C. 154(b) by 1243 days.

(21) Appl. No.: 10/927,772

(22) Filed: Aug. 26, 2004

(65) Prior Publication Data

US 2006/0058678 A1 Mar. 16, 2006

(51) Int. Cl.
*A61B 8/14* (2006.01)

(52) U.S. Cl. .............. 600/459; 601/2; 600/439

(58) Field of Classification Search .......... 601/2–4; 600/407–480

See application file for complete search history.

(56) References Cited

U.S. PATENT DOCUMENTS

| | | | | |
|---|---|---|---|---|
| 2,795,709 A * | 6/1957 | Camp | | 310/337 |
| 3,142,035 A * | 7/1964 | Harris | | 367/155 |
| 3,942,150 A | 3/1976 | Booth et al. | | |
| 3,974,475 A | 8/1976 | Burckhardt et al. | | |
| 3,992,693 A * | 11/1976 | Martin et al. | | 367/155 |
| 4,000,493 A | 12/1976 | Spaulding et al. | | |
| 4,074,564 A * | 2/1978 | Anderson | | 73/618 |
| 4,206,653 A * | 6/1980 | LeMay | | 73/602 |
| 4,221,132 A | 9/1980 | Poole | | |
| 4,307,613 A | 12/1981 | Fox | | |
| 4,339,952 A | 7/1982 | Foster | | |
| 4,454,597 A | 6/1984 | Sullivan | | |
| 4,478,083 A | 10/1984 | Hassler et al. | | |
| 4,505,156 A | 3/1985 | Questo | | |
| 4,526,168 A | 7/1985 | Hassler et al. | | |
| 4,537,074 A | 8/1985 | Dietz | | |
| 4,549,533 A | 10/1985 | Cain et al. | | |
| 4,554,925 A | 11/1985 | Young | | |
| 4,662,222 A * | 5/1987 | Johnson | | 73/602 |
| 4,817,614 A | 4/1989 | Hassler et al. | | |
| 4,858,597 A | 8/1989 | Kurtze et al. | | |
| 4,865,042 A | 9/1989 | Umemura et al. | | |

(Continued)

FOREIGN PATENT DOCUMENTS

DE 4345308 C2 2/2001
EP 0031614 A1 7/1981

(Continued)

OTHER PUBLICATIONS

Huber, Peter, et al. "A New Noninvasive Approach in Breast Cancer Therapy Using Magnetic Resonance Imaging-Guided Focused Ultrasound Surgery" Cancer Research 61, 8441-8447, Dec. 1, 2001.

(Continued)

*Primary Examiner* — Brian Casler
*Assistant Examiner* — Amanda Lauritzen
(74) *Attorney, Agent, or Firm* — Bingham McCutchen LLP (57) ABSTRACT

A focused ultrasound system includes an ultrasound transducer device forming an opening, and having a plurality of transducer elements positioned at least partially around the opening. A focused ultrasound system includes a structure having a first end for allowing an object to be inserted and a second end for allowing the object to exit, and a plurality of transducer elements coupled to the structure, the transducer elements located relative to each other in a formation that at least partially define an opening, wherein the transducer elements are configured to emit acoustic energy that converges at a focal zone.

35 Claims, 4 Drawing Sheets

U.S. PATENT DOCUMENTS

| | | | |
|---|---|---|---|
| 4,888,746 A | 12/1989 | Wurster et al. | |
| 4,889,122 A | 12/1989 | Watmough et al. | |
| 4,893,284 A | 1/1990 | Magrane | |
| 4,893,624 A | 1/1990 | Lele | |
| 4,937,767 A | 6/1990 | Reuschel et al. | |
| 5,197,475 A | 3/1993 | Antich et al. | |
| 5,209,221 A | 5/1993 | Riedlinger | |
| 5,211,160 A * | 5/1993 | Talish et al. | 601/2 |
| 5,247,935 A | 9/1993 | Cline et al. | |
| 5,271,400 A | 12/1993 | Dumoulin et al. | |
| 5,275,165 A | 1/1994 | Ettinger et al. | |
| 5,291,890 A | 3/1994 | Cline et al. | |
| 5,307,812 A | 5/1994 | Hardy et al. | |
| 5,307,816 A | 5/1994 | Hashimoto et al. | |
| 5,318,025 A | 6/1994 | Dumoulin et al. | |
| 5,323,779 A | 6/1994 | Hardy et al. | |
| 5,327,884 A | 7/1994 | Hardy et al. | |
| 5,329,930 A | 7/1994 | Thomas, III et al. | |
| 5,368,031 A | 11/1994 | Cline et al. | |
| 5,368,032 A | 11/1994 | Cline et al. | |
| 5,379,642 A | 1/1995 | Reckwerdt et al. | |
| 5,391,140 A | 2/1995 | Schaetzle et al. | |
| 5,413,550 A | 5/1995 | Castel | |
| 5,435,312 A * | 7/1995 | Spivey et al. | 600/448 |
| 5,443,068 A | 8/1995 | Cline et al. | |
| 5,474,071 A | 12/1995 | Chapelon et al. | |
| 5,485,839 A | 1/1996 | Aida et al. | |
| 5,490,840 A | 2/1996 | Uzgiris et al. | |
| 5,507,790 A | 4/1996 | Weiss | |
| 5,520,188 A | 5/1996 | Hennige et al. | |
| 5,520,612 A | 5/1996 | Winder et al. | |
| 5,526,814 A | 6/1996 | Cline et al. | |
| 5,549,638 A | 8/1996 | Burdette | |
| 5,553,618 A | 9/1996 | Suzuki et al. | |
| 5,573,497 A | 11/1996 | Chapelon | |
| 5,582,578 A | 12/1996 | Zhong et al. | |
| 5,590,653 A | 1/1997 | Aida et al. | |
| 5,590,657 A | 1/1997 | Cain et al. | |
| 5,601,526 A | 2/1997 | Chapelon et al. | |
| 5,605,154 A | 2/1997 | Ries et al. | |
| 5,606,971 A | 3/1997 | Sarvazyan | |
| 5,617,371 A | 4/1997 | Williams | |
| 5,617,857 A | 4/1997 | Chader et al. | |
| 5,643,179 A | 7/1997 | Fujimoto | |
| 5,662,170 A | 9/1997 | Donovan et al. | |
| 5,665,054 A | 9/1997 | Dory | |
| 5,666,954 A | 9/1997 | Chapelon et al. | |
| 5,676,673 A | 10/1997 | Ferre et al. | |
| 5,687,729 A | 11/1997 | Schaetzle | |
| 5,694,936 A | 12/1997 | Fujimoto et al. | |
| 5,711,300 A | 1/1998 | Schneider et al. | |
| 5,722,411 A | 3/1998 | Suzuki et al. | |
| 5,728,062 A | 3/1998 | Brisken | |
| 5,739,625 A * | 4/1998 | Falcus | 310/328 |
| 5,743,863 A | 4/1998 | Chapelon | |
| 5,752,515 A | 5/1998 | Jolesz et al. | |
| 5,759,162 A | 6/1998 | Oppelt et al. | |
| 5,762,616 A * | 6/1998 | Talish | 601/2 |
| 5,769,790 A | 6/1998 | Watkins et al. | |
| 5,810,008 A | 9/1998 | Dekel et al. | |
| 5,810,731 A | 9/1998 | Sarvazyan et al. | |
| 5,873,845 A | 2/1999 | Cline et al. | |
| 5,897,495 A | 4/1999 | Aida et al. | |
| 5,904,659 A | 5/1999 | Duarte et al. | |
| 5,938,600 A | 8/1999 | Van Vaals et al. | |
| 5,938,608 A | 8/1999 | Bieger et al. | |
| 5,947,900 A | 9/1999 | Derbyshire et al. | |
| 5,984,881 A | 11/1999 | Ishibashi et al. | |
| 6,004,269 A | 12/1999 | Crowley et al. | |
| 6,023,636 A | 2/2000 | Wendt et al. | |
| 6,042,556 A | 3/2000 | Beach et al. | |
| 6,071,239 A | 6/2000 | Cribbs et al. | |
| 6,113,559 A | 9/2000 | Klopotek | |
| 6,128,522 A | 10/2000 | Acker et al. | |
| 6,128,958 A | 10/2000 | Cain | |
| 6,135,960 A | 10/2000 | Holmberg | |
| 6,193,659 B1 | 2/2001 | Ramamurthy et al. | |
| 6,217,530 B1 | 4/2001 | Martin et al. | |
| 6,242,915 B1 | 6/2001 | Hurd | |
| 6,246,895 B1 | 6/2001 | Plewes | |
| 6,246,896 B1 | 6/2001 | Dumoulin et al. | |
| 6,263,230 B1 | 7/2001 | Haynor et al. | |
| 6,267,734 B1 | 7/2001 | Ishibashi et al. | |
| 6,289,233 B1 | 9/2001 | Dumoulin et al. | |
| 6,309,355 B1 | 10/2001 | Cain et al. | |
| 6,317,619 B1 | 11/2001 | Boernert et al. | |
| 6,322,527 B1 * | 11/2001 | Talish | 601/2 |
| 6,334,846 B1 | 1/2002 | Ishibashi et al. | |
| 6,374,132 B1 | 4/2002 | Acker et al. | |
| 6,392,330 B1 | 5/2002 | Zloter et al. | |
| 6,397,094 B1 | 5/2002 | Ludeke et al. | |
| 6,413,216 B1 | 7/2002 | Cain et al. | |
| 6,419,648 B1 * | 7/2002 | Vitek et al. | 601/3 |
| 6,424,597 B1 | 7/2002 | Bolomey et al. | |
| 6,425,867 B1 | 7/2002 | Vaezy et al. | |
| 6,428,532 B1 | 8/2002 | Doukas et al. | |
| 6,433,464 B2 | 8/2002 | Jones | |
| 6,461,314 B1 | 10/2002 | Pant et al. | |
| 6,475,150 B2 * | 11/2002 | Haddad | 600/448 |
| 6,478,739 B1 * | 11/2002 | Hong | 600/437 |
| 6,506,154 B1 * | 1/2003 | Ezion et al. | 600/437 |
| 6,506,171 B1 * | 1/2003 | Vitek et al. | 601/2 |
| 6,508,774 B1 | 1/2003 | Acker et al. | |
| 6,511,428 B1 | 1/2003 | Azuma et al. | |
| 6,522,142 B1 | 2/2003 | Freundlich et al. | |
| 6,524,251 B2 | 2/2003 | Robiner et al. | |
| 6,543,272 B1 * | 4/2003 | Vitek | 73/1.83 |
| 6,559,644 B2 | 5/2003 | Froundlich et al. | |
| 6,566,878 B1 | 5/2003 | Komura et al. | |
| 6,582,381 B1 | 6/2003 | Yehezkeli et al. | |
| 6,599,256 B1 | 7/2003 | Acker et al. | |
| 6,612,988 B2 | 9/2003 | Maor et al. | |
| 6,613,004 B1 | 9/2003 | Vitek et al. | |
| 6,613,005 B1 * | 9/2003 | Friedman et al. | 601/2 |
| 6,618,608 B1 | 9/2003 | Watkins et al. | |
| 6,618,620 B1 * | 9/2003 | Freundlich et al. | 607/27 |
| 6,626,854 B2 * | 9/2003 | Friedman et al. | 601/2 |
| 6,626,855 B1 | 9/2003 | Weng et al. | |
| 6,629,929 B1 | 10/2003 | Jago et al. | |
| 6,645,162 B2 * | 11/2003 | Friedman et al. | 601/2 |
| 6,652,461 B1 * | 11/2003 | Levkovitz | 600/443 |
| 6,666,833 B1 | 12/2003 | Friedman et al. | |
| 6,676,601 B1 | 1/2004 | Lacoste et al. | |
| 6,676,602 B1 | 1/2004 | Barnes et al. | |
| 6,679,855 B2 | 1/2004 | Horn et al. | |
| 6,705,994 B2 * | 3/2004 | Vortman et al. | 600/443 |
| 6,719,694 B2 | 4/2004 | Weng et al. | |
| 6,733,450 B1 | 5/2004 | Alexandrov et al. | |
| 6,735,461 B2 * | 5/2004 | Vitek et al. | 600/411 |
| 6,761,691 B2 | 7/2004 | Tsuzuki | |
| 6,770,031 B2 | 8/2004 | Hynynen et al. | |
| 6,770,039 B2 | 8/2004 | Zhong et al. | |
| 6,788,619 B2 | 9/2004 | Calvert | |
| 6,790,180 B2 * | 9/2004 | Vitek | 600/438 |
| 6,824,516 B2 | 11/2004 | Batten et al. | |
| 6,951,540 B2 | 10/2005 | Ebbini et al. | |
| 6,961,606 B2 * | 11/2005 | DeSilets et al. | 600/415 |
| 7,001,379 B2 | 2/2006 | Behl et al. | |
| 7,077,820 B1 | 7/2006 | Kadziauskas et al. | |
| 7,094,205 B2 * | 8/2006 | Marmarelis | 600/448 |
| 7,128,711 B2 | 10/2006 | Medan et al. | |
| 7,155,271 B2 | 12/2006 | Halperin et al. | |
| 7,175,596 B2 | 2/2007 | Vitek et al. | |
| 7,175,599 B2 | 2/2007 | Hynynen et al. | |
| 7,264,592 B2 * | 9/2007 | Shehada | 600/444 |
| 7,264,597 B2 | 9/2007 | Cathignol | |
| 7,344,509 B2 | 3/2008 | Hynynen et al. | |
| 7,377,900 B2 | 5/2008 | Vitek et al. | |
| 7,429,248 B1 | 9/2008 | Winder et al. | |
| 7,452,357 B2 | 11/2008 | Vlegele et al. | |
| 7,505,805 B2 | 3/2009 | Kuroda | |
| 7,505,808 B2 | 3/2009 | Anderson et al. | |
| 7,507,213 B2 | 3/2009 | Schultheiss et al. | |
| 7,510,536 B2 | 3/2009 | Foley et al. | |
| 7,511,501 B2 | 3/2009 | Wexler | |
| 7,535,794 B2 | 5/2009 | Prus et al. | |
| 7,553,284 B2 | 6/2009 | Vaitekunas | |

| | | |
|---|---|---|
| 7,611,462 B2 | 11/2009 | Vortman et al. |
| 7,652,410 B2 | 1/2010 | Prus |
| 7,699,780 B2 | 4/2010 | Vitek et al. |
| 2001/0031922 A1 | 10/2001 | Weng et al. |
| 2002/0016557 A1 | 2/2002 | Duarte et al. |
| 2002/0035779 A1 | 3/2002 | Krieg et al. |
| 2002/0082589 A1 | 6/2002 | Friedman et al. |
| 2002/0095087 A1 | 7/2002 | Mourad et al. |
| 2002/0111552 A1 | 8/2002 | Maor et al. |
| 2002/0161300 A1 | 10/2002 | Hoff et al. |
| 2002/0188229 A1* | 12/2002 | Ryaby et al. ............ 601/2 |
| 2003/0004439 A1 | 1/2003 | Pant et al. |
| 2003/0060820 A1 | 3/2003 | Maguire et al. |
| 2004/0030251 A1 | 2/2004 | Ebbini et al. |
| 2004/0059265 A1 | 3/2004 | Candy et al. |
| 2004/0068186 A1 | 4/2004 | Ishida et al. |
| 2004/0116809 A1* | 6/2004 | Chow et al. ............ 600/439 |
| 2004/0122316 A1 | 6/2004 | Satoh |
| 2004/0122323 A1 | 6/2004 | Vortman et al. |
| 2004/0143187 A1 | 7/2004 | Biagi et al. |
| 2004/0210134 A1 | 10/2004 | Hynynen et al. |
| 2004/0210135 A1 | 10/2004 | Hynynen et al. |
| 2004/0236253 A1 | 11/2004 | Vortman et al. |
| 2004/0267126 A1 | 12/2004 | Takeuchi |
| 2005/0033201 A1* | 2/2005 | Takahashi et al. ........ 601/2 |
| 2005/0096542 A1 | 5/2005 | Weng et al. |
| 2005/0131301 A1 | 6/2005 | Peszynski et al. |
| 2005/0199058 A1* | 9/2005 | Danz et al. ............ 73/455 |
| 2005/0203444 A1 | 9/2005 | Schonenberger et al. |
| 2005/0251046 A1* | 11/2005 | Yamamoto et al. ...... 600/459 |
| 2006/0052661 A1 | 3/2006 | Gannot et al. |
| 2006/0052701 A1 | 3/2006 | Carter et al. |
| 2006/0052706 A1 | 3/2006 | Hynynen et al. |
| 2006/0058671 A1 | 3/2006 | Vitek et al. |
| 2006/0058678 A1 | 3/2006 | Vitek et al. |
| 2006/0106300 A1 | 5/2006 | Seppenwoolde et al. |
| 2006/0173307 A1* | 8/2006 | Amara et al. .......... 600/437 |
| 2006/0173385 A1* | 8/2006 | Lidgren et al. .......... 601/2 |
| 2006/0184034 A1 | 8/2006 | Haim et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2007/0016039 A1 | 1/2007 | Vortman et al. |
| 2007/0055140 A1 | 3/2007 | Kuroda |
| 2007/0066897 A1* | 3/2007 | Sekins et al. .......... 600/437 |
| 2007/0073135 A1 | 3/2007 | Lee et al. |
| 2007/0098232 A1 | 5/2007 | Matula et al. |
| 2007/0167781 A1 | 7/2007 | Vortman et al. |
| 2007/0167798 A1 | 7/2007 | Cai et al. |
| 2007/0197918 A1 | 8/2007 | Vitek et al. |
| 2007/0219470 A1* | 9/2007 | Talish et al. ............ 601/2 |
| 2007/0239062 A1 | 10/2007 | Chopra et al. |
| 2007/0265560 A1 | 11/2007 | Soltani et al. |
| 2007/0276237 A1 | 11/2007 | Li |
| 2008/0027342 A1 | 1/2008 | Rouw et al. |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0108900 A1* | 5/2008 | Lee et al. ............ 600/459 |
| 2008/0125660 A1 | 5/2008 | Yao et al. |
| 2008/0183077 A1 | 7/2008 | Moreau-Gobard |
| 2008/0228081 A1 | 9/2008 | Becker et al. |
| 2008/0312562 A1* | 12/2008 | Routh et al. ............ 601/2 |
| 2009/0088623 A1 | 4/2009 | Vortman et al. |
| 2009/0118619 A1 | 5/2009 | Oshiki |
| 2010/0030076 A1 | 2/2010 | Vortman et al. |
| 2010/0056962 A1 | 3/2010 | Vortman et al. |
| 2010/0125193 A1 | 5/2010 | Zadicario |
| 2010/0179425 A1 | 7/2010 | Zadicario |
| 2010/0268088 A1 | 10/2010 | Prus et al. |
| 2010/0318002 A1 | 12/2010 | Prus et al. |
| 2011/0066032 A1 | 3/2011 | Vitek et al. |
| 2011/0094288 A1 | 4/2011 | Medan et al. |

FOREIGN PATENT DOCUMENTS

| | | |
|---|---|---|
| EP | 0320303 | 6/1989 |
| EP | 0558029 | 9/1993 |
| EP | 0558029 A2 | 9/1993 |
| EP | 0875203 A2 | 11/1998 |
| EP | 1132054 | 9/2001 |
| EP | 1591073 | 11/2005 |
| EP | 174920 | 4/2007 |
| EP | 1790384 | 5/2007 |
| EP | 1936404 | 6/2008 |
| FR | 2806611 | 9/2001 |
| JP | 5-92008 | 4/1993 |
| JP | 7-184907 | 7/1995 |
| JP | 7-231895 | 9/1995 |
| JP | 7-313518 | 12/1995 |
| JP | 11313833 A | 11/1999 |
| JP | 00/166940 | 6/2000 |
| JP | 01/516075 | 9/2001 |
| JP | 02/530145 | 9/2002 |
| WO | WO-9100059 A1 | 1/1991 |
| WO | WO-95/14505 | 6/1995 |
| WO | WO-9852465 A1 | 11/1998 |
| WO | WO-00/31614 | 6/2000 |
| WO | WO-0166189 A1 | 9/2001 |
| WO | WO-01/80709 | 11/2001 |
| WO | WO-0180709 A2 | 11/2001 |
| WO | WO-02/43805 | 6/2002 |
| WO | WO-02/44753 | 6/2002 |
| WO | WO-02058791 A1 | 8/2002 |
| WO | WO-03/013654 | 2/2003 |
| WO | WO-03097162 A2 | 11/2003 |
| WO | WO-03098232 A2 | 11/2003 |
| WO | WO-2004/093686 | 11/2004 |
| WO | WO-2006/018837 | 2/2006 |
| WO | WO-2006/021851 | 3/2006 |
| WO | WO-2006025001 A1 | 3/2006 |
| WO | WO-2006087649 A1 | 8/2006 |
| WO | WO-2006/119572 | 11/2006 |
| WO | WO-2007/051066 | 5/2007 |
| WO | WO-2007073551 A1 | 6/2007 |
| WO | WO-2008/039449 | 4/2008 |
| WO | WO-2008050278 A1 | 5/2008 |
| WO | WO-2008119054 A1 | 10/2008 |
| WO | WO-2009055587 A1 | 4/2009 |
| WO | WO-2009/081339 | 7/2009 |
| WO | WO-2010/058292 | 5/2010 |
| WO | WO-2010/082135 | 7/2010 |
| WO | WO-2010/119340 | 10/2010 |
| WO | WO-2010/143072 | 12/2010 |
| WO | WO-2011/013001 | 2/2011 |
| WO | WO-2011/024074 | 3/2011 |
| WO | WO-2011/045669 | 4/2011 |

OTHER PUBLICATIONS

Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).

Cain et al., "Concentric-ring and Sector-vortex Phased-array Applicators for Ultrasound Hperthermia," IEEE Trans. On Microwave Theory & Techniques, vol. MTT-34, No. 5, pp. 542-551 (May 1986).

Chen et al., "MR Acoustic Radiation Force Imaging: Comparison of Encoding Gradients."

Cline et al., "Focused US system for MR imaging-guide tumor ablation," Radiology, v. 194, No. 3, pp. 731-738 (Mar. 1995).

Cline et al., "MR Temperature mapping of focused ultrasound surgery," Magnetic Resonance in Medicine, vol. 32, No. 6, pp. 628-636 (1994).

Cline et al., "Simultaneous magnetic resonance phase and magnitude temperature maps in muscle," Magnetic Resonance in Medicine, vol. 35, No. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

de Senneville et al., "Real-time adaptive methods for treatment of mobile organs by MRI-controlled high-intensity focussed Ultrasound," Magnetic Resonance in Medicine 57:319-330 (2007).

Fjield et al, "The Combined Concentric-ring and Sector-vortex Phased Array for MRI Guided Ultrasound Surgery," IEEE Trans. On Ultrasonics, Ferroelectrics and Freq. Cont., vol. 44, No. 5, pp. 1157-1167 (Sep. 1997).

Herbert et al., "Energy-based adaptive focusing of waves: application to ultrasonic transcranial therapy," 8th Intl. Symp. On Therapeutic Ultrasound.

International Preliminary Report on Patentability in International Patent Application No. PCT/IB2004/001512, mailed Dec. 8, 2005.

International Search Report and Written Opinion in International Patent Application No. PCT/IB2004/001498, dated Aug. 31, 2004.

International Search Report and Written Opinion in International Patent Application No. PCT/IB2005/002273, mailed Dec. 20, 2005.

International Search Report and Written Opinion in International Patent Application No. PCT/IB2006/001641, mailed Sep. 25, 2006.

International Search Report and Written Opinion in International Patent Application No. PCT/IB2006/003300, mailed Feb. 14, 2008.

International Search Report and Written Opinion in International Patent Application No. PCT/IB2007/001079, mailed Dec. 10, 2007.

International Search Report and Written Opinion in International Patent Application No. PCT/IB2007/002134, mailed Dec. 13, 2007.

International Search Report and Written Opinion in International Patent Application No. PCT/IB2007/002140, mailed Dec. 29, 2008.

International Search Report and Written Opinion in International Patent Application No. PCT/IB2008/003069, mailed Apr. 27, 2009.

Jolesz et al., "Integration of interventional MRI with computer-assisted surgery," J. Magnetic Resonance Imaging. 12:69-77 (2001).

Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).

Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).

Maxwell et al., "Noninvasive thrombolysis using pulsed ultrasound cavitation therapy—Histotripsy," Abstract, U.S. Natl. Lib. Of Med., NIH, Ultrasound Med. Biol. (Oct. 23, 2009).

McDannold et al., "MRI evaluation of thermal ablation of tumors and focused ultrasounds," JMRI vol. 8, No. 1, pp. 91-100 (1998).

McDannold et al., "Magnetic resonance acoustic radiation force imaging," Med. Phys. vol. 35, No. 8, pp. 3748-3758 (Aug. 2008).

Medel et al., "Sonothrombolysis: An emerging modality for the management of stroke," Neurosurgery, vol. 65, No. 5, pp. 979-993.

Mougenot et al., "MR monitoring of the near-field HIFU heating," 8th Intl. Symp. On Therapeutic Ultrasound, edited by E.S. Ebbini, U. of Minn. (Sep. 2009).

Partial International Search Report and Written Opinion in International Patent Application No. PCT/IB2007/001079, dated Sep. 25, 2007.

Vimeux et al., "Real-time control of focused ultrasound heating based on rapid MR thermometry," Investig. Radiology, vol. 43, No. 3, pp. 190-193.

Vykhodtseva et al., "MRI detection of the thermal effects of focused ultrasound on the brain," Ultrasound in Med. & Biol., vol. 26, No. 5, pp. 871-880 (2000).

Written Opinion in International Patent Application No. PCT/IL01/00340, mailed Feb. 24, 2003.

Written Opinion in International Patent Application No. PCT/IL02/00477, mailed Feb. 25, 2003.

Written Opinion in International Patent Application No. PCT/IB03/05551, mailed Sep. 10, 2004.

"How is Ablatherm treatment performed?" http://www.edap-hifu.com/eng/physicians/hifu/3c_treatment_treat-description.htm, accessed Jan. 3, 2003.

"What is HIFU? HIFU: High Intensity Focused Ultrasound," http://www.edap-hifu.com/eng/physicians/hifu2a_hifu_overview.htm, accessed Jan. 3, 2003.

"What are the physical principles?" http://www.edap-hifu.com/eng/physicians/hifu/2c_hifu_physical.htm, accessed Jan. 3, 2003.

"How does HIFU create a lesion?" http://www.edap-hifu.com/eng/physicians/hifu/2d_hifu_lesion.htm, accessed Jan. 3, 2003.

"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.

"Abstract" Focus Surgery, http://www.focus-surgery.com/Sanghvi.htm, accessed Jan. 3, 2003.

Exablate 2000 Specification, InSightec, Ltd. (2 pages).

FDA Approves Exablate 2000 as Non-invasive surgery for Fibroids, Oct. 22, 2004.

PCT International Search Report for PCT/IB2005 /002413, Applicant: Insightec-Image Guided, Forms PCT/ISA/220 & PCT/ISA/210, dated Nov. 22, 2005 (7 pages).

PCT Written Opinion for PCT/IB2005 /002413, Applicant: Insightec-Image Guided, Forms PCT/ISA/237, dated Nov. 22, 2005 (5 pages).

McGough et al., "Direct Computation of Ultrasound Phased-Array Driving Signals from a Specified Temperature Distribution for Hyperthermia," IEEE Transactions on Biomedical Engineering, vol. 39, No. 8, pp. 825-835 (Aug. 1992).

McDonnald et al. "Usefulness of MR Imaging-Derived Thermometry and Dosimetry in Determining the Threshold for Tissue Damage INduced by Thermal Surgery in Rabbits," Radiology, vol. 216, No. 2000 pp. 517-523 (2000).

Suprijanto et al. "Displacement Correction Scheme for MR-Guided Interstitial Laser Therapy," Ellis RE, Peters TM (Eds.): MiCCAI, LNCS 2879, pp. 399-407 (2003).

Shmatukha et al. "Correction of Proton Resonance Frequencey Shift Temperature Maps for Magnetic Field Disturbances Caused by Breathing," Physics in Medicine and Biology, vol. 51, No. 18 pp. 4689-4705 (2006).

De Senneville et al., "An Optimised Multi-Baseline Approach for On-Line MR-Temperature Monitoring on Commodity Graphics Hardware," Biomedical Imaging, pp. 1513-1516 (2008).

Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).

Fronheiser et al., "3D Acoustic Radiation Force Impulse (ARFI) Imaging Using a 2D Matrix Array: Feasibility Study," Ultrasonics Symposium, pp. 1144-1147 (Oct. 2006).

Wu et al., "MR Imaging of Shear Waves Generated by Focused Ultrasound," Magnetic Resonance in Medicine, vol. 43, pp. 111-115 (2000).

Heikkila et al., "Simulations of Lesion Detection Using a Combined Phased Array LHMI-Technique,"Ultrasonics, IPC Science and Technology Press Ltd., vol. 48, No. 6-7, pp. 568-573 (Nov. 2008).

* cited by examiner

FOCUSED ULTRASOUND SYSTEM FOR SURROUNDING A BODY TISSUE MASS AND TREATMENT METHOD

FIELD OF INVENTION

The present invention relates generally to apparatus and methods for delivering diagnostic and/or therapeutic ultrasound energy from a transducer disposed outside a body.

BACKGROUND

Devices and systems using acoustic energy, particularly within the ultrasonic range, i.e., acoustic waves with a frequency greater than about twenty kilohertz (20 kHz), and more typically between fifty kiloHertz and ten MegaHertz (0.05-10 MHz), have been used to diagnose and treat patients. Ultrasonic energy may be employed to obtain images of a patient during a diagnostic or therapeutic procedure. In addition, ultrasound systems have been used for treating tissue, e.g., by directing acoustic energy towards a target tissue region within a patient, such as a cancerous or benign tumor, to coagulate, necrose, generate mechanical damage (by cavitation) or otherwise heat the tissue region. For example, one or more piezoelectric transducers may be disposed adjacent a patient's body and used to deliver high intensity acoustic waves, such as ultrasonic waves, at an internal tissue region of a patient to treat the tissue region. An exemplary focused ultrasound system is disclosed in U.S. Pat. No. 4,865,042 issued to Umemura et al. The acoustic energy emitted from such a system may be focused at a desired focal zone to deliver thermal energy to the target tissue region.

Focused ultrasound procedures may allow a patient to be treated while avoiding invasive surgery. For example, a focused ultrasound system that includes a single concave transducer has been used to treat breast, uterine and other tumors. Such transducer transmits an acoustic beam, which converges into a focus in target tissue to treat tissue. However, the acoustic beam may transverse through an organ, such as a breast nipple, or other sensitive areas, either before the beam converges into the focus (i.e., in a near field) or beyond the target tissue (i.e., in a far field). These areas have a high absorption coefficient compared to regular tissue, thereby risking damage to non targeted tissue at the near field and/or the far field. Also, in some cases, the acoustic beam may impinge on a tissue (e.g., bone tissue) that would not allow the beam to pass through by reflecting and/or absorbing most of the impinging energy. As a result, the acoustic beam may not reach the target tissue, and may generate undesired heating at the tissue surface that is blocking or interfering the acoustic beam. In some cases, the heating of bone tissue may also heat, and adversely affect, a nerve that is adjacent the bone tissue. A similar situation could happen with volumes in the body that are filled with air acting as total reflector for acoustic beam, thereby blocking the beam from propagating to the target tissue region.

Certain physical anatomy, e.g., a breast or an arm, can impose special problems in positioning an ultrasound transducer to effectively direct the ultrasound energy at the target tissue mass (e.g., a tumor underlying a nipple, or along one side of a bone), while reducing the risk of adversely impacting nearby healthy tissue.

SUMMARY OF THE INVENTION

In one embodiment of the invention, a focused ultrasound system includes an ultrasound transducer device forming an opening, the ultrasound device having a plurality of transducer elements positioned at least partially around the opening.

In another embodiment, a focused ultrasound system includes a structure having a first end configured to allow an object to be inserted there through, and a second end configured for allowing the object to exit there through, the structure defining an aperture, and a plurality of transducer elements coupled to the structure, the transducer elements positioned relative to each other in a formation such that acoustic energy emitted from the transducer elements converges at a focal zone located in the aperture.

In yet another embodiment, a method of treating body tissue with ultrasound energy includes positioning a part of the body containing the tissue to be treated within an aperture defined by a transducer device, the transducer device having a plurality of acoustic transducer elements positioned in a formation about the aperture, and providing drive signals to cause one or more of the transducer elements to emit acoustic energy focused in one or more focal zones in the tissue to be treated.

Other aspects, features and embodiments of the invention will be evident from reading the following detailed description of the illustrated embodiments, which are intended to illustrate, and not to limit, the invention.

BRIEF DESCRIPTION OF THE DRAWINGS

Various embodiments of the invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention, and are not intended as an exhaustive description of, or as a limitation on, the scope of the invention. In addition, aspects or features described in conjunction with a particular embodiment of the invention are is not necessarily limited to that embodiment, and may be applicable in other embodiments.

DETAILED DESCRIPTION OF THE ILLUSTRATED EMBODIMENTS

Figure 1A:
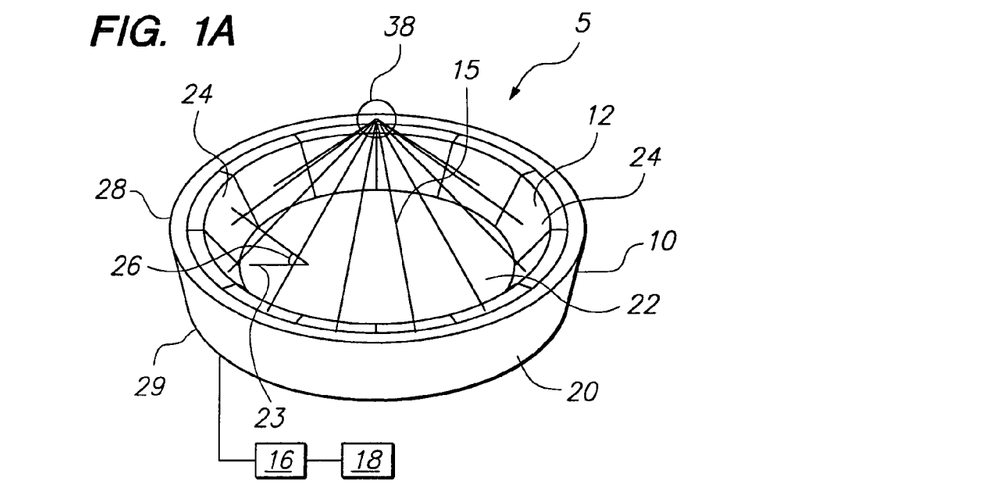
FIG. 1A illustrates an ultrasound system having a transducer device in accordance with some embodiments of the invention.

FIG. 1A illustrates a focused ultrasound system 5 that includes a transducer device 10 constructed in accordance with some embodiments of the invention. The focused ultrasound system 5 includes a drive circuitry 16 coupled to the transducer device 10, and a controller 18 coupled to the drive circuitry 16. The transducer device 10 is configured to deliver acoustic energy (represented by beam 15) to a target tissue region located inside a patient. The acoustic energy 15 may be used to coagulate, necrose, heat, or otherwise treat the target tissue region, which may be a benign or malignant tumor within an organ or other tissue structure (not shown).

Figure 2:
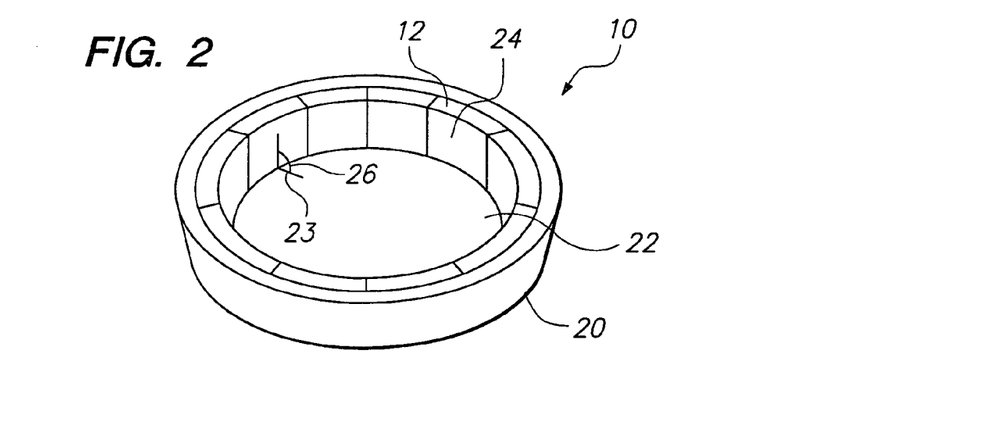
FIG. 2 illustrates a transducer device in accordance with still other embodiments of the invention.

In the illustrated embodiments, the transducer device 10 includes a structure 20 and a plurality of transducer elements 12 secured to the structure 20. The transducer elements 12 are positioned in an arrangement or formation to thereby define an opening 22. During use, the opening 22 allows at least a portion of an object, such as a breast, be inserted from a first side 28 of the transducer device 10 and exit from a second side 29 of the transducer device 10. For examples, the opening 22 can have a cross sectional dimension that is between 50 cm to 100 cm (e.g., for accommodating a body), or between 10 cm to 50 cm (e.g., for accommodating a breast, an arm, a leg, or a head). Although the arrangement of the transducer elements 12 is shown to have a closed ring-configuration, in other embodiments, the arrangement can have an opened ring-configuration or a partial ring configuration. Also, instead of arranging the transducer elements 12 in a slanted orientation to form a partial conical configuration, in other embodiments, the transducer elements 12 can be oriented in a partial tube configuration (FIG. 2). In the illustrated embodiments, the arrangement of the transducer elements 12 has a circular ring-like configuration. Alternatively, the arrangement of the transducer elements 12 can also have a variety of shapes, such as an elliptical ring-shape, a rectangular ring-shape, or other customized shapes (e.g., a conformal shape that will follow the body contour within a tolerance). In the illustrated embodiments, the structure 20 has a ring-like configuration, but alternatively, can also have other shapes, forms, and/or configurations so long as it is capable of providing a platform or area to which the transducer elements 12 can be secured. The structure 20 may be substantially rigid, semi-rigid, or substantially flexible, and can be made from a variety of materials, such as plastics, polymers, metals, and alloys. The structure 20 can be manufactured as a single unit, or alternatively, be assembled from a plurality of components that are parts of the transducer device 10. Electrodes and conducting wires (not shown) may also be provided in a known manner for coupling the transducer elements 12 to the driver 16. The electrodes for the transducer elements 12 are preferably housed within the structure 20, and exit from the structure 20 for coupling to the driver 16 and/or the controller 18.

The transducer elements 12 are coupled to the driver 16 and/or controller 18 for generating and/or controlling the acoustic energy emitted by the transducer elements 12. For example, the driver 16 may generate one or more electronic drive signals, which may be controlled by the controller 18. The transducer elements 12 convert the drive signals into acoustic energy 15, which may be focused using conventional methods. The controller 18 and/or driver 16 may be separate or integral components. It will be appreciated by one skilled in the art that the operations performed by the controller 18 and/or driver 16 may be performed by one or more controllers, processors, and/or other electronic components, including software and/or hardware components. The terms controller and control circuitry may be used herein interchangeably, and the terms driver and drive circuitry may be used herein interchangeably.

The driver 16, which may be an electrical oscillator, may generate drive signals in the ultrasound frequency spectrum, e.g., as low as twenty kilohertz (20 KHz), and as high as ten Megahertz (10 MHz). Preferably, the driver 16 provides drive signals to the transducer elements 12 at radio frequencies (RF), for example, between about 100 Kilohertz to ten Megahertz (0.1-10 MHz), and more preferably between about two hundreds Kilohertz and three Megahertz (0.2 and 3.0 MHz), which corresponds to wavelengths in tissue of approximately 7.5 to 0.5 mm. However, in other embodiments, the driver 16 can also be configured to operate in other ranges of frequencies. When the drive signals are provided to the transducer elements 12, the transducer elements 12 emit acoustic energy 15 from its exposed surface, as is well known to those skilled in the art.

The controller 18 may control the amplitude, and therefore the intensity or power of the acoustic waves transmitted by the transducer elements 12. The controller 18 may also control a phase component of the drive signals to respective transducer elements 12 of the transducer device 10, e.g., to control a shape of a focal zone 38 generated by the transducer elements 12 and/or to move the focal zone 38 to a desired location. For example, as is well known to those skilled in the art, the location of the focus can be determined by adjusting the phases of the individual elements in such a way that constructive interference is generated at the desired location, provided the sizes of the individual elements are small enough to allow significant contribution to the energy at the focus at high steering angles and keep aberrations at an acceptable level.

As explained above, the transducer elements 12 convert the drive signals into acoustic energy, represented by energy beam 15. As the acoustic energy 15 passes through the patient's body, the acoustic energy 15 is absorbed in the tissue and converted to heat in the pass zone and at the focal zone within target region thereby raising the temperature of tissue within the target region. The tissue temperature rise depends on the intensity (energy/$cm^2$) in situ. The acoustic energy 15 may be focused on the target region to raise the temperature of the tissue to coagulate the tissue while minimizing damage to surrounding healthy tissue. Exemplary apparatus for measuring and/or calibrating the energy output of a transducer device are described in U.S. patent application Ser. No. 10/005,845, filed Dec. 3, 2001. The disclosure of this application and any references cited therein are expressly incorporated herein by reference.

In the illustrated embodiments, each of the transducer elements 12 may be a one-piece piezoceramic part, or alternatively, be composed of a mosaic arrangement of a plurality of small piezoceramic elements (e.g., phased array). The piezoceramic parts or the piezoceramic elements may have a variety of geometric shapes, such as hexagons, triangles, squares, and the like.

The transducer elements 12 can be individually controlled to change, e.g., a respective phase and/or amplitude of the respective acoustic waves in order to create a desired focal zone. If the transducer elements 12 include a plurality of piezoceramic elements, each of the piezoceramic elements may be coupled to a respective timing or delay element. The timing or delay elements may be implemented as a part of the ultrasound transducer device 10, the driver 16, or the controller 18.

In the illustrated embodiments, the transducer elements 12 are arranged in a formation about a circumference of the opening 22, and each transducer element 12 has a surface 24 that forms an angle 26 with a plane 23 in which the structure 20 approximately lies. In the example shown in FIG. 1A, the angle 26 is approximately 30°, but can also be other angles, such as 60° or 90° (FIG. 2), in other embodiments. Also, in the illustrated embodiments, the transducer elements 12 are fixedly secured to the structure 20 such that the angle 26 does not vary during use. In other embodiments, the transducer elements 12 can be rotatably secured to the structure 20 such that the angle 26 can be adjusted during use. In such cases, the transducer device 10 further includes a positioner for moving the transducer elements 12. The positioner can, for examples, include a motor, such as an electric motor or piezoelectric motor, a hydraulic, or a gimbal system, for changing the angle 26. In some embodiments, the structure 20 can include a plurality of movable sections to which one or more of the transducer elements 12 are secured. In such cases, the movable sections are installed on respective gimbals, and the transducer elements 12 are movable by operation of the gimbals. Also, in other embodiments, instead of positioning the transducer elements 12 in one degree of freedom, the transducer elements 12 can configured to move in multiple degree of freedoms (e.g., two or up to six degree of freedoms relative to the opening 26).

Figure 1B:
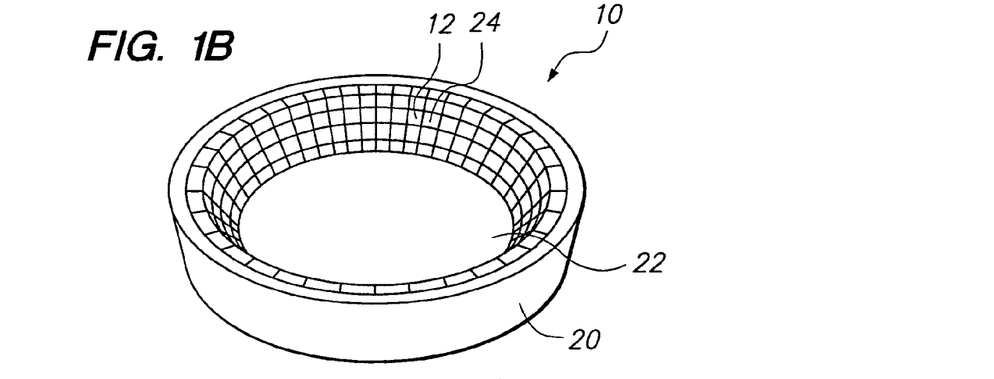
FIG. 1B illustrates a transducer device having a plurality of rows of transducer elements in accordance with other embodiments of the invention.

In the illustrated embodiments, the transducer device 10 includes a single row (ring) of transducer elements 12. However, the scope of the invention should not be so limited. In alternative embodiments, the transducer device 10 can include a plurality of rows (e.g., adjacent rings) of transducer elements 12 (FIG. 1B). As shown in FIG. 1B, the transducer device 10 has four rows/rings of transducer elements 12, with each ring having twenty-nine transducer elements 12 for focusing and steering the beam. In some embodiments, the opening has a 10 cm cross sectional dimension, and the number of transducer elements 12 per ring could be 300 to 700. It should be noted that the number of rows (rings) of transducer elements 12, and the number of transducer elements 12 per row should not be limited to that shown in the example, and that in alternative embodiments, the transducer device 10 can have other numbers of rows and other numbers of transducer elements per row.

Figure 3:
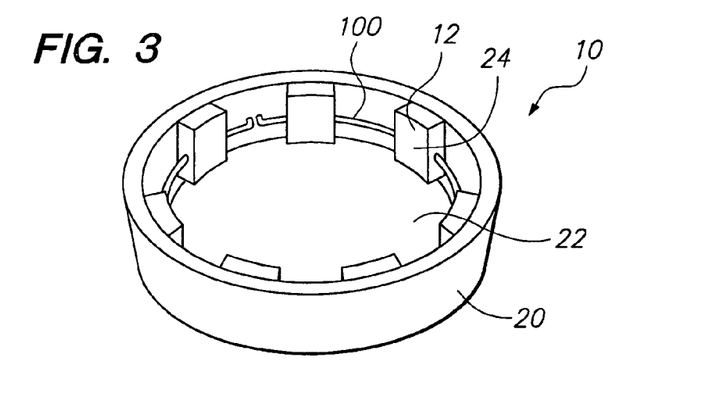
FIG. 3 illustrates a transducer device in accordance with yet further embodiments of the invention, showing the transducer device having spaced apart transducer elements.

In the illustrated embodiments, the transducer elements 12 of the transducer device 10 substantially abut against adjacent transducer elements 12 such that the transducer elements 12 collectively define a substantially complete opening. In other embodiments, the transducer elements 12 can be spaced apart from adjacent transducer elements 12 to partially define the opening 22 (FIG. 3). Such configuration may be beneficial because, while it still allows acoustic energy from different angles to converge, it reduces the number of transducer elements 12, thereby reducing cost. Also, the spacing between adjacent transducer elements 12 can be used to house mechanical and/or electrical components of the transducer device 10. In the illustrated embodiments, the transducer device 10 further includes a guide rail 100 to which the transducer elements 12 are slidably coupled. Such configuration allows the positions of the transducer elements 12 about the perimeter of the opening 22 be adjusted by sliding the transducer elements 12 along the guide rail 100. The transducer elements 12 can also be movably coupled to the structure 20 using other mechanical joints, connections, and configurations. In other embodiments, the transducer elements 12 are fixedly secured to the structure 20, in which cases, the transducer device 10 does not include the guide rail 100 or similar mechanisms.

Figure 4:
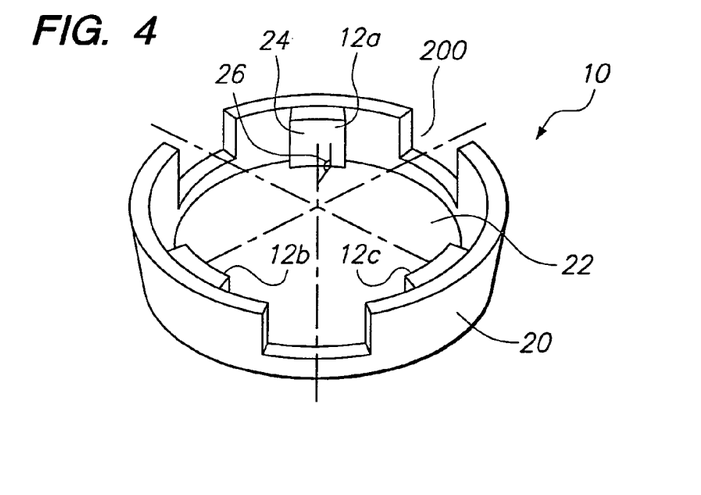
FIG. 4 illustrates a transducer device in accordance with still further embodiments of the invention, showing the transducer device having transducer elements that do not face each other.

Also, in other embodiments, the transducer elements 12 can be so positioned such that each of the transducer elements 12 does not face another transducer elements 12 (FIG. 4). As shown in FIG. 4, the transducer device 10 includes three transducer elements 12a-12c, with each transducer element 12 having a surface 24 that forms approximately a 90° angle 26 with the plane 23. Alternatively, the angle 26 can be different from 90°. Although three transducer elements 12 are shown, in other embodiments, the transducer device 10 can have more or less than three transducer elements 12. In the illustrated embodiments, the transducer elements 12a-12c do not face each other, thereby allowing beam emerging from respective surfaces 24 of the transducer elements 12 to pass through the spacing between the transducer elements 12. Such configuration has the advantage of preventing emerging beam from one transducer element from damaging another (e.g., opposing) transducer element. Such configuration also prevents beam emitted by one transducer element from being reflected by another transducer element. Also, in the illustrated embodiments, the structure 10 includes a plurality of openings 200 that allow beams emitted by the transducer elements 12 to exit, thereby preventing the beams from being reflected by the structure 10. Although the openings 200 are each shown to have a shape that resembles a rectangle, in other embodiments, the openings 200 can have other shapes. Also, in other embodiments, the transducer elements 12a-c are oriented at an angle (such as that similarly shown in FIG. 1A), in which cases, the openings 200 can provide a similar advantage as that discussed previously.

Figure 5:
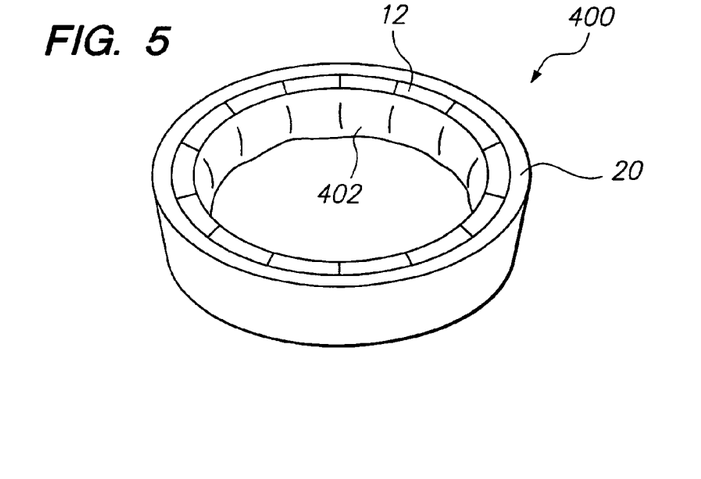
FIG. 5 illustrates a transducer device in accordance with yet further embodiments of the invention, showing the transducer device having a coupling membrane.

Any embodiments of the transducer device described herein can further include a coupling membrane. FIG. 5 illustrates a transducer device 400 in accordance with other embodiments of the invention. The transducer device 400 is similar to the transducer device 10 of FIG. 1A except that it further includes a coupling membrane 402. The coupling membrane 402 can be, for examples, an inflatable body or a balloon. The coupling membrane 402 has an opening (not shown) adapted for receiving a medium for inflation of the membrane 402. After the coupling membrane 402 is inflated by the medium, it may be used to press against a surface of an object for acoustic coupling. The medium may be a liquid acoustic propagation medium for propagating or transmitting generated ultrasound from the transducer elements 12. The coupling membrane 402 and the medium preferably exhibit an acoustic impedance that essentially corresponds to that of body tissue. For example, the coupling membrane 402 is preferably made from a polymer or a rubber, and degassed water is preferably used as the medium. During use, the coupling membrane 402 provides or improves an acoustic coupling between the transducer elements 12 and an object, such as a skin of a patient, while focused ultrasound energy is being delivered. In some embodiments, a cool medium can be used to inflate and/or circulate within the coupling membrane 402, thereby preventing excessive heat from being created at an interface between the coupling membrane 402 and a patient's skin, or by the transducer.

Figure 6:
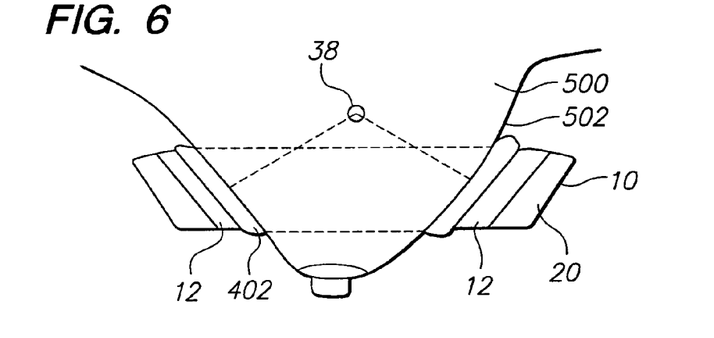
FIG. 6 illustrates a method for treating breast tissue using the transducer device of FIG. 1A.

Referring to FIG. 6, a method of using the system 5 will now be described with reference to a treatment of tissue within a breast 500. First, a coupling gel is applied on a breast skin 502. If the transducer device 10 includes the coupling membrane 402, the coupling membrane 402 is then inflated With a medium, such as degassed water. Next, the breast 500 is at least partially inserted into the opening 22 such that the transducer elements 12 at least partially circumscribe a portion of the breast 500. In the illustrated embodiments, the transducer device 10 is secured to a patient support (not shown) having an opening. The patient support supports the patient in a face-down position, while the opening of the patient support allows the patient's breast 500 to exit and be placed on the transducer device 10. In other embodiments, the transducer device 10 can be secured to a frame in an upright position such that the patient's breast 500 can be placed onto the transducer device 10 while the patient is in his/her upright position. Also, in other embodiments, the transducer device 10 can be implemented as a hand-held instrument, thereby allowing a physician to place the transducer device 10 onto the patient.

If the transducer elements 12 are movable relative to the structure 20, the position and/or the orientation of the transducer elements 12 can be adjusted. After the transducer elements 12 have been desirably positioned relative to the breast 500, the transducer device 10 then delivers focused ultrasound energy to target tissue within the breast 500. As can be appreciated by those skilled in the art, delivering focused ultrasound energy from a wide angle (e.g., from different positions around the breast 500) increases the surface area of the breast skin 502 through which beam energy from the transducer elements 12 is passing. This, in turn, prevents, or at least reduces the risk of, excessive energy density at a patient's skin and tissue, thereby preventing injury to the patient's skin or non targeted tissue. Also, because beam energy is being delivered from the transducer elements 12 in a direction that is not directly towards a rib cage (e.g., beam energy is delivered in a direction approximately parallel to the rib cage), heating of the rib cage is prevented or at least reduced.

During the procedure, the driver 16 and/or the controller 18 may be used to generate and/or to control the acoustic energy emitted by the transducer device 10. For example, the driver 16 and/or the controller 18 can control a phase of the transducer elements 12 to thereby adjust a position of the focal zone 38 and/or to change a shape of the focal zone 38 during use. If the transducer device 10 includes the positioner for moving the transducer elements 12, the driver 16 and/or the controller 18 can be used to control the positioner to thereby adjust the position and/or shape of the focal zone. In some embodiments, the driver 16 and/or the controller 18 can cause the transducer elements 12 to deliver beam(s) for creating multiple focal zones 38, thereby allowing treatment of multiple target region simultaneously.

Also, in some embodiments, a feedback mechanism is provided to measure one or more of a size, shape, location, and intensity of the focal zone 38. For example, MRI simultaneous thermal imaging can be used to thermally map the focal zones. The measured size, shape, location, or density is then compared (e.g., by human operator or a processor, such as that described in U.S. Pat. No. 6,618,620) with a desired size, shape, location, or intensity, respectively, of the focal zone 38. Based on the comparison, the phase and/or amplitude of the drive signals is changed to adjust a size, shape, location, and/or intensity of the focal zone 38. In other embodiments, a position of one or more of the transducer elements 12 can be changed in response to a result of the comparison.

After a desired amount of ultrasound energy has been delivered, the breast 500 is then removed from the transducer device 10, or vice versa.

Figure 7:
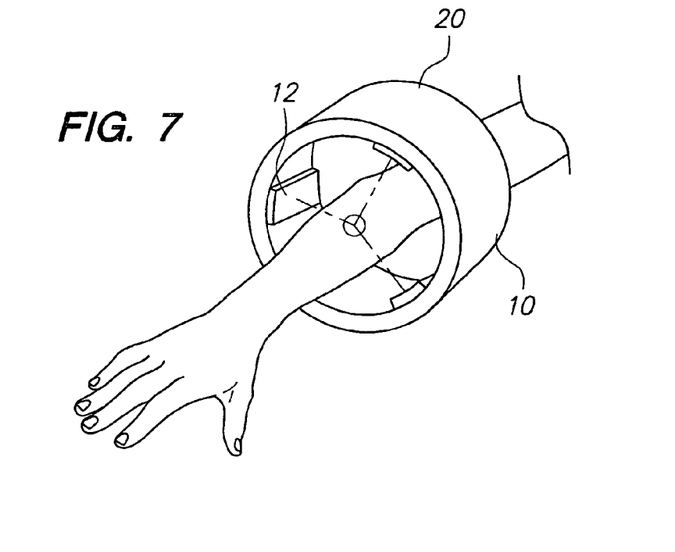
FIG. 7 illustrates a method for treating tissue within an arm using the transducer device of FIG. 1A.
Figure 8:
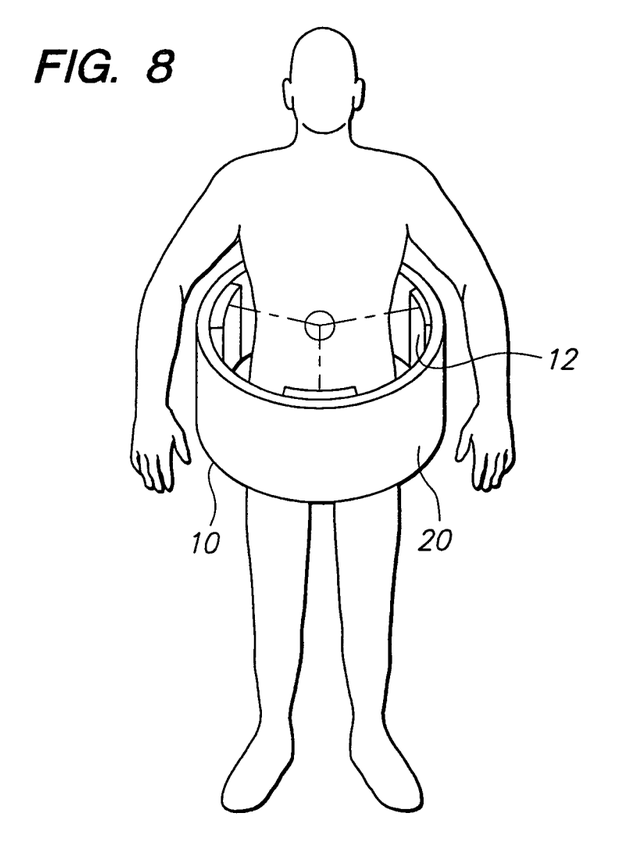
FIG. 8 illustrates a method for treating tissue within a body using the transducer device of FIG. 1A.
Figure 9:
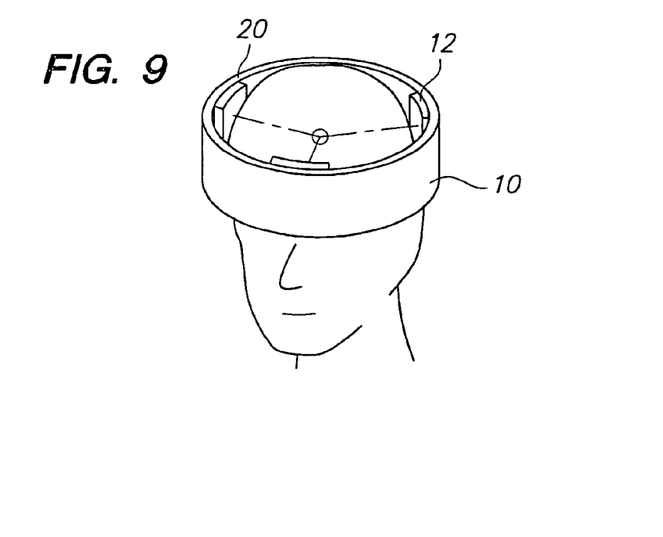
FIG. 9 illustrates a method for treating tissue within a head using the transducer device of FIG. 1A.

Although the above method has been described with reference to treating tissue within a breast, any of the transducer devices described herein can also be used to treat tissue at other locations of the body. For examples, the transducer device can be used to treat tissue within an arm (FIG. 7), within a body (FIG. 8), or within a head (FIG. 9) of a patient. As shown in FIGS. 7-9, delivering focused ultrasound energy from a wide angle (e.g., from different positions around the arm, the body, or the head) increases the surface area of the skin to which beam energy from the transducer elements is directed, and decreases energy density in the tissue pass zone. This, in turn, prevents, or at least reduces the risk of, excessive energy density at a patient's skin, at internal sensitive organs, or at bony surfaces, at the far field, thereby preventing injury to the patient's skin or internal non targeted organs. Any of the ultrasound devices described herein may also be used to treat tissues at other parts of a body, such as bone tissue, muscle tissue, tissue within a neck, or brain tissue. Besides treating tissue, the same ultrasound device may also be used to deliver diagnostic ultrasound for imaging tissue.

Further, in other embodiments, any of the transducer devices described herein can be coupled to a positioner for controlling a position of the transducer device relative to a patient. For example, the transducer device 10 of FIG. 8 can be positioned by a positioner to move along a length of the arm to treat different tissue, including bone tissue, along the arm. Similarly, the transducer devices 10 of FIGS. 8 and 9 can be positioned along the body and the head, respectively, to treat different tissue, or the beam could be steered electronically using transducer elements phase control.

Although particular embodiments of the invention have been shown and described, it should be understood that the above discussion is not intended to limit the invention to these embodiments.

What is claimed:

1. A focused ultrasound system configured for treatment of a body part, comprising:
    an ultrasound transducer device having a ring configuration and forming an opening sized to allow a portion of the body to pass through and exit the opening, the ultrasound device having a plurality of transducer elements positioned at least partially around an inward facing surface of the ring configuration; and
    a controller for operating the transducer elements to focus ultrasound waves transmitted by the transducer elements,
    wherein the transducer elements are arranged at an angle in a slanted orientation to form a partial conical configuration so as to prevent the transmitted ultrasound waves from damaging any of the transducer elements during operation.

2. The system of claim 1, wherein the opening has a cross sectional dimension between 5 cm and 100 cm.

3. The system of claim 1, wherein the opening has a cross sectional dimension that allows at least a part of an object to be accommodated therein.

4. The system of claim 3, wherein the opening is configured to accommodate an object selected from the group consisting of a breast, an arm, a leg, a body, a neck, and a head.

5. The system of claim 1, wherein each one of the plurality of the transducer elements abuts against another one of the plurality of the transducer elements.

6. The system of claim 1, wherein each one of the plurality of the transducer elements is spaced from other ones of the plurality of transducer elements.

7. The system of claim 1, wherein the opening has a shape that is approximately circular.

8. The system of claim 1, wherein the opening has a shape that resembles a polygon.

9. The system of claim 1, wherein the opening has a shape, at least a portion of the shape having a contour that resembles a part of a body contour.

10. The system of claim 9, further comprising a positioner for positioning one or more of the plurality of the transducer elements relative to another one or more of the plurality of transducer elements.

11. The system of claim 10, wherein the positioner comprises a gimbal system.

12. The system of claim 10, wherein the positioner comprises a piezoelectric motor.

13. The system of claim 1, wherein the plurality of transducer elements are time-delayed drive.

14. The system of claim 1, wherein the plurality of transducer elements are phase-delayed driven.

15. The system of claim 1, further comprising a coupling membrane coupled to the ultrasound transducer device.

16. The system of claim 1, wherein the transducer elements are arranged in a plurality of rows.

17. The focused ultrasound system of claim 1, wherein the ultrasound transducer device is hand-held.

18. The focused ultrasound system of claim 17 further comprising a support arm into which the ring configuration is secured.

19. A method of treating body tissue with ultrasound energy, comprising:
   passing a portion of a body part through an ultrasound transducer device having a ring configuration forming an opening, the ultrasound transducer device having a plurality of transducer elements positioned at least partially around an inward facing surface of the ring configuration; and
   at least one of configuring or operating the transducer elements to transmit ultrasound waves focused at a location outside a volume surrounded by the ring configuration so as to prevent damage to any of the transducer elements during operation.

20. The method of claim 19, further comprising selecting respective phases, amplitudes, or both, of drive signals after the body part is positioned in the opening in order to determine one or more of a size, shape, location and intensity of one or more focal zones.

21. The method of claim 19, further comprising moving one or more of the transducer elements after the body part is positioned in the opening in order to determine one or more of a size, shape, location and intensity of one or more focal zones.

22. The method of claim 19, wherein the opening has a circular shape.

23. The method of claim 19, wherein the opening has a ellipsoidal shape.

24. The method of claim 19, wherein the opening has a polygonal shape.

25. The method of claim 19, further comprising measuring one or more of a size, shape, location and intensity of one or more focal zones, and determining a difference between a measured size, shape, location, or intensity, and a desired size, shape, location, or intensity, respectively, of the one or more focal zones.

26. The method of claim 25, further comprising changing a position of one or more of the transducer elements relative to other of the transducer elements in response to a determined difference between a measured and desired size, shape, location, or intensity of the one or more focal zones.

27. The method of claim 25, further comprising changing one or both of a phase and amplitude of one or more drive signals in response to a determined difference between a measured and desired size, shape, location, or intensity of the one or more focal zones.

28. The method of claim 19, wherein operating the transducer elements comprises controlling respective phases of the transducer elements to focus the ultrasound waves at a location outside the volume surrounded by the ring.

29. The method of claim 19, wherein configuring the transducer elements comprises adjusting an angle of the transducer elements so as to focus the ultrasound waves at a location outside the volume surrounded by the ring.

30. The method of claim 19, wherein configuring the transducer elements comprises adjusting positions of the transducer elements about a perimeter of the opening such that each transducer element does not face another transducer element during operation.

31. The method of claim 30, wherein adjusting the positions comprises positioning the transducer elements opposite openings in the transducer device.

32. The method of claim 30, wherein adjusting the positions comprises sliding the transducer elements along a guide rail mounted to the ring configuration along a perimeter of the opening.

33. A focused ultrasound system configured for treatment of a body part, comprising:
   an ultrasound transducer device having a ring configuration and forming an opening sized to allow a portion of the body to pass through and exit the opening, the ultrasound device having a plurality of transducer elements positioned at least partially around an inward facing surface of the ring configuration; and
   a controller for operating the transducer elements to focus ultrasound waves transmitted by the transducer elements,
   wherein the transducer elements are positioned and spaced so as to not oppose one another in a fixed arrangement, such that the transmitted ultrasound waves are prevented from damaging any of the transducer elements.

34. The focused ultrasound system of claim 33, wherein the ultrasound transducer device comprises openings opposite the transducer elements.

35. The focused ultrasounds system of claim 33, wherein the transducer elements are slidably coupled to a guide rail along a perimeter of the opening of the ring configuration.

* * * * *